United States Patent [19]

Woodin, Jr. et al.

[11] Patent Number: 5,494,533

[45] Date of Patent: Feb. 27, 1996

[54] METHOD FOR PERSONAL CLEANSING

[75] Inventors: Frederick W. Woodin, Jr., Naugatuck; George E. Deckner, Trumbull, both of Conn.

[73] Assignee: Richardson-Vicks, Inc., Shelton, Conn.

[21] Appl. No.: 182,464

[22] Filed: Jan. 14, 1994

Related U.S. Application Data

[63] Continuation of Ser. No. 25,907, Mar. 3, 1993, abandoned, which is a continuation of Ser. No. 806,564, Dec. 12, 1991, abandoned.

[51] Int. Cl.$^6$ .............................. B08B 7/00; C11D 17/00
[52] U.S. Cl. ..................... 134/40; 252/174; 252/174.23; 252/DIG. 2; 252/DIG. 4
[58] Field of Search ........................ 252/174.23, 174.17, 252/DIG. 2, DIG. 14, DIG. 5; 424/47; 514/859, 828; 134/40

[56] References Cited

U.S. PATENT DOCUMENTS

| | | | |
|---|---|---|---|
| 4,269,824 | 5/1981 | Villamarin et al. . | |
| 4,514,385 | 4/1985 | Damani et al. | 424/81 |
| 4,663,158 | 5/1987 | Wolfram et al. . | |
| 4,683,004 | 7/1987 | Goddard | 424/47 |
| 4,690,818 | 9/1987 | Puchalski et al. . | |
| 4,725,433 | 2/1988 | Matravers . | |
| 4,871,530 | 10/1989 | Grollier et al. | 424/47 |
| 4,876,083 | 10/1989 | Grollier et al. . | |
| 4,954,332 | 9/1990 | Bissett et al. . | |
| 4,963,535 | 10/1990 | Sebag et al. . | |
| 5,011,681 | 4/1991 | Ciotti et al. . | |
| 5,028,263 | 7/1991 | Burdick . | |
| 5,076,953 | 12/1991 | Jordan et al. | 252/108 |

FOREIGN PATENT DOCUMENTS

| | | |
|---|---|---|
| 0353987 | 2/1990 | European Pat. Off. . |
| 395332 | 10/1990 | European Pat. Off. . |
| 9114759 | 10/1991 | WIPO . |

OTHER PUBLICATIONS

Jones, R. T. et al. "The Behavior of Cationic Cellulose Derivatives Containing Fatty Quat Groups", Int. J. Cosmet. Sci., 10(5), pp. 219–229, 1988.

Domsch, A. et al. "Cationic Protein Derivatives for Hair Cosmetics", CA 110(6):44731h.

Kawai, et al. "Shampoos Containing Sulfosuccinates" CA 114(26):253841r (1990).

Lion Corp, "Liq. skin detergent compsn. with good foaming" Derwent Abs. No. 90–236134/31 (1990).

*Primary Examiner*—George Fourson
*Assistant Examiner*—C. Everhart
*Attorney, Agent, or Firm*—David K. Dabbiere; Anthony D. Sabatelli; Leonard W. Lewis

[57] ABSTRACT

The present invention relates to a method for personal cleansing with rinse-off compositions comprising certain foam enhancing polymers in an aqueous solvent system. These compositions, when delivered from an aerosol or non-aerosol system, produce aesthetically preferred foam in copious amounts.

17 Claims, No Drawings

METHOD FOR PERSONAL CLEANSING

This is a continuation of application Ser. No. 08/025,907, filed on Mar. 3, 1993 now abandoned which is a continuation of application Ser. No. 806,564, filed on Dec. 12, 1991.

FIELD OF THE INVENTION

This invention pertains to personal cleansing and shaving compositions for personal washing/shaving, especially of the face.

BACKGROUND OF THE INVENTION

Foaming cosmetic compositions must satisfy a number of criteria including cleansing power, foaming properties and especially mildness/low irritancy with respect to the skin, hair and the occular mucosae.

Skin is made up of several layers of cells which coat and protect the keratin and collagen fibrous proteins that form the skeleton of its structure. The outermost of these layers, referred to as the stratum corneum, is known to be composed of 250 A diameter protein bundles surrounded by 80 A thick bilayers of epidermal lipids and water. Surfactants can penetrate the stratum corneum membrane and, by delipidization (i.e. removal of the lipids from the stratum corneum), destroy its integrity. This destruction of the stratum corneum bilayers can lead to dry rough skin and may eventually permit the surfactant to interact with the viable epidermis, creating irritation.

Ideal cosmetic cleansers should cleanse the skin or hair gently, causing little or no irritation without defatting and or drying the skin and without leaving skin taut after frequent use. Most lathering soaps, liquids, gels and bars are limited in this respect due to their use of surfactants.

Thus a need exists for foaming cosmetic compositions which will produce a foam which is abundant, stable and of high quality (compactness), which are effective skin and hair cleansers and which are very mild to the skin, hair and occular mucosae.

Liquid and solid bar compositions based on soap and/or synthetic surfactants are commonly used for cleansing the human body. To achieve adequate lather when diluted with water, these require a higher level of surfactant than may be necessary to provide adequate cleaning. This excess surfactant can be irritating to the skin and is put into the environment unnecessarily. The use of foams for cleaning skin has usually been reserved for specialty products that are used without rinsing. See, e.g., U.S. Pat. No. 3,962,150, Viola, issued Jun. 8, 1976, incorporated herein by reference. There has been little or no recognition of the mildness and environmental advantages that can be derived from the use of such products for general cleansing.

Personal cleansing compositions exist today in a variety of product forms. These forms range from emollient and lathering cleansers to cold creams and bar soaps. The commonality of each of these forms is that they always contain some level of soap and/or synthetic surfactant components (detergents).

Surfactant based cleansing systems typically contain a combination of surfactant and polymer components. The polymer additions are primarily recognized, and have been extensively documented, for their ability to provide skin and/or hair conditioning properties. These polymers are further recognized for their ability to reduce the inherent skin irritancy properties of surfactants. The polymer components reduce skin irritation by developing a protective barrier on the skin surface that inhibits delipidization and the resultant barrier destruction properties of surfactants. Barrier destruction has been documented to be a primary contributor to dermal irritation. The polymer components are further recognized for their ability to enhance the foaming properties of emollient and lathering cleanser forms as well as bar soaps. Polymers are known to alter the physical properties (i.e. density/stability) and textural properties (i.e. creaminess) of foams. Combinations of polymers and surfactants have been, and continue to be used today to produce personal cleansing compositions that provide the cleansing and foaming properties necessary to attain consumer appeal. However, it has not before been recognized that compositions which do not contain a cleansing level of surfactant can provide very mild cleansing compositions.

The present invention relates to aerated personal cleansing compositions that provide cleansing efficacy without the use of any surfactant components. The polymer(s) system can also include at least one anionic, nonionic, or amphoteric alkyl substituent to the backbone of the polymeric carbon chain. Because of the absence of any irritating surfactants, these compositions are extremely mild to skin and/or hair.

A further object of the invention is to deposit hydrophilic agents, such as sunscreen agents to skin and/or hair. Such deposition of sunscreen agents would provide protection from the chronic damaging effects associated with ultraviolet exposure. The instant invention further encompasses the use of cosmetic astringents to provide oil removal/control properties to the skin. The invention further encompasses the use of polymer based cleansing systems to optionally deposit, for example, hydrophilic emollient and/or humectant components, and to provide moisturization and hydration properties to the skin.

SUMMARY OF THE INVENTION

The present invention relates to a method for personal cleansing with rinse-off compositions comprising certain foam enhancing polymers in an aqueous solvent system. Said compositions, when delivered from an aerosol or non-aerosol system, produce aesthetically preferred foam in copious amounts.

All concentrations and ratios herein are by weight of total composition and all measurements are at 25° C., unless otherwise specified.

DETAILED DESCRIPTION OF THE INVENTION

The present invention comprises a method for personal cleansing comprising applying to the skin or hair a rinse-off cleansing composition substantially-free of a surfactant comprising: (a) from about 0.01% to about 20% by weight of a viscosity enhancing water-soluble polymer having a molecular weight of from about 1,000 to about 3,000,000 wherein said viscosity enhancing polymer accounts for a rise in the viscosity of the composition (without the polymer) of at least about 1 centipoise, and (b) from about 80% to about 99.8% water.

The composition of this invention preferably has a viscosity of at least about 0.1 to about 150, more preferably from about 20 to about 60, and even more preferably from about 20 to about 50 centipoise at 25° C. when measured using a Brookfield RVT Viscometer equipped with spindle #1 at 100 rpm. In general, the upper viscosity limit is as high as can be tolerated as long as the product can be easily dispensed; thus viscosities of 20, 30, and even 40 cps are included within the scope of this invention.

Compared to personal cleansing compositions that are in the form of toilet bars, the compositions of the present invention are extremely mild. The use of no detergent surfactant makes the invention milder than systems that contain detergent surfactants. The aerated form of the product provides a foam that is desirable to the consumer and provides cleansing without the need to use aggressive detergent surfactants to improve foaming.

From an environmental standpoint, as discussed hereinbefore, the invention uses little or no detergent materials therefore reducing the environmental impact of detergent pollutants.

The compositions of this invention comprise from about 20% to about 99% water, preferably at least about 50%, water, and a minor amount of other suitable solvents. Higher levels of water and lower levels of organic materials are desirable to minimize environmental concern.

The Polymers

It has been discovered that certain polymeric cleansing compositions that are designed to be foamed via mechanical force e.g., in a squeeze foamer container, as described in detail hereinafter, can provide cleansing as well. In general, the useful polymers must be soluble in water to a level that will give the desired viscosity increase. Suitable polymers are those which contain an alkyl radical containing about 8 to about 30 carbon atoms. These polymers are high molecular weight materials (mass-average molecular weight determined, for instance, by light scattering), being generally from about 1,000 to about 3,000,000, preferably from about 1,000 to about 150,000, and more preferably from about 5,000 to about 100,000. Since the polymers apparently operate by raising the viscosity of the compositions, the polymers preferably have a thickening ability such that a 1% dispersion of the polymer in water at about 21° C. (70° F.) exceeds about 1 centipoise, preferably about 2 centipoise. Useful polymers are the cationic, nonionic, amphoteric, and anionic polymers useful in the cosmetic field. Preferred are cationic and nonionic resins and mixtures thereof, especially those that are beneficial to the skin and/or hair. Also preferred are cellulose derivatives such as hydroxyethyl- and carboxymethylcellulose and guar gums such as hydroxypropyltrimethylammonium guar gum.

The cationic polymers most preferred in the present invention are those preferably having a polymer backbone selected from the group consisting of cellulose, cellulose derivatives, polyacrylamides, proteins, hydrolyzed proteins, and mixtures thereof. Specific examples of such polymers useful in the present invention include, but are not limited to, laurdimonium hydroxyethyl cellulose (available as Crodacel QL from Croda), lauryldimonium hydroxypropyl hydrolyzed collagen (available as Lamequat L from Grunau), lauryldimonium hydroxypropyl hydrolyzed casein (available as Promois Milk-LAQ from Seiwa Kasei), lauryldimonium hydroxypropyl hydrolyzed keratin (available as Promois WK-HLAQ from Seiwa Kasei), lauryldimonium hydroxypropyl hydrolyzed silk (available as Promois Silk-LAW from Seiwa Kasei), lauryl dimonium hydroxyprorpyl hydrolyzed soy protein (available as quat-Soy LDMA-25 from Brooks), polyquaternium-11 (available as Gafquat 755 from GAF) and mixtures thereof. Especially preferred are laurdimonium hydroxyethyl cellulose and lauryldimonium hydroxypropyl hydrolyzed collagen, and mixtures thereof. Even more preferred is the mixture of lauryldimonium hydroxypropyl hydrolyzed collagen laurdimonium hydroxyethyl cellulose and in a weight ratio of from about 2:1 to about 1:2, most preferably in a weight ratio of approximately 1:1.

Personal cleansing products containing quaternary amine polymers are disclosed in one or more of the following patents:

| Pat. No. | Date | Inventor(s) |
| --- | --- | --- |
| U.S. 3,761,418 | 9/1973 | Parran, Jr.; |
| U.S. 4,234,464 | 11/1980 | Morshauser; |
| U.S. 4,061,602 | 12/1977 | Oberstar et al.; |
| U.S. 4,472,297 | 9/1984 | Bolich et al.; |
| U.S. 4,491,539 | 1/1985 | Hoskins et al.; |
| U.S. 4,540,507 | 9/1985 | Grollier; |
| U.S. 4,673,525 | 6/1987 | Small et al.; |
| U.S. 4,704,244 | 11/1987 | Saud; and |
| Jap. J57105 | 6/30/82 | Pola. |

All of the above patents are incorporated herein by reference, especially for their basic personal cleansing product and polymer disclosures.

As stated above, the polymers useful herein are any of the typical polymers that provide the required increase in viscosity. The substituted cellulose materials preferred herein are commonly found in detergent compositions and are suitable for use in compositions that come in contact with the skin. Especially preferred are the substituted cellulose polymers that are readily water-soluble or water-dispersible, and especially those that form clear solutions when used at low levels. Examples of such polymers are the carboxymethyl- and ethoxylated cellulose polymers.

Specific examples include: hydroxyethyl cellulose (e.g., Natrosol 250MXR, Natrosol 250HR, etc.); and cationic cellulose polymers (e.g., Union Carbide's JR-400).

Other anionic, nonionic, and cationic polymeric skin conditioning agents useful in the present invention have molecular weights of from 1,000 to 3,000,000. Useful polymers are selected from the group consisting of:

(I) nonionic, anionic, and cationic polysaccharides;

(II) copolymers of the saccharides of (I) and compatible synthetic monomers;

(III) synthetic water-soluble polymers containing water-soluble groups, e.g., quaternized silicones and quaternized polycarboxylates.

Specific examples of members of the cationic polysaccharide class include the cationic hydroxyethyl cellulose, e.g., JR-400 and LM-200 made by Union Carbide Corporation.

Copolymers of saccharides and synthetic monomers useful in the present invention encompass those containing the following saccharides: glucose, galactose, mannose, arabinose, xylose, fucose, fructose, glucosamine, galactosamine, glucuronic acid, galacturonic acid, and 5 or 6 membered ring polyalcohols. Xanthan gum, e.g., Keltrol T, (molecular weight about 2,000,000) is also a suitable polymer. Also included are hydroxymethyl, hydroxyethyl and hydroxypropyl derivatives of the above sugars.

Other desirable polymers are the bulky amine polymers as defined in the copending U.S. Patent Application of Robert G. Bartolo and Louis F. Wong, Ser. No. 07/374,315 filed Jun. 30, 1989 pending, for "PERSONAL CLEANSING PRODUCT WITH ODOR COMPATIBLE BULKY CATIONIC POLYMER," said application being incorporated herein by reference. Such polymers have the following generalized formula in which the backbone is represented by "POLYMER" and having the indicated non-labile cationic functional group:

(I) (POLYMER)-$(CR^1H\text{—}CR^2R^3\text{—}NR^4R^5R^6)_x$ wherein $R^1$-$R^3$ is H or any other substituent and $R^4$, $R^5$ and $R^6$ combine with N to form an amine with less odor impact than trimethylamine, preferably at least one of $R^4$, $R^5$ and $R^6$ is alkyl having a chain length of from about 2 to about 24 carbon atoms, or an alkoxyalkyl group containing from about 2 to about 12 carbon atoms.

Some examples of preferred bulky amine polymers are cationic guar gums having the following structures, wherein "guar" represents the guar gum backbone:

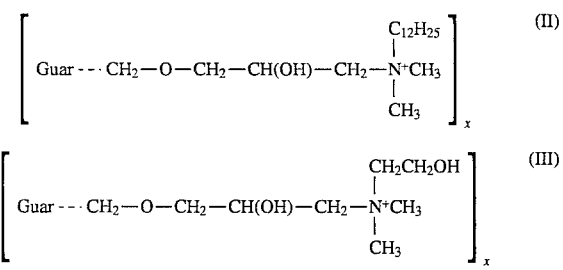

An example of a bulky amine hydroxyethyl cellulose (HEC) polymer is:

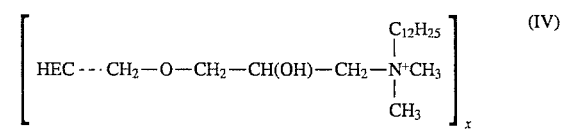

The "x" in the above formulae is typically selected to provide a degree of substitution of from about 0.5 to about 4, preferably from about 1 to about 2.5. These "bulky amine" groups have no odor problem and also have improved skin conditioning benefits.

The composition of this invention preferably comprises from about 0.01% to about 20%, preferably from about 5% to about 10%, of the polymer. Some preferred cationic guars (galactomannans) are disclosed in U.S. Pat. No. 4,758,282, Stober et al., issued Jul. 19, 1988, incorporated herein by reference. The cationic guar gum polymers disclosed in commonly assigned U.S. patent application Ser. No. 07/456,065 now U.S. Pat. No. 4,946,618, J. R. Knochel and P. E. Vest, filed Dec. 21, 1989, incorporated by reference herein, are suitable, especially when the cationic groups are substituted with bulky amine groups.

Some additional polymers include polyvinylpyrrolidone and copolymers of vinylpyrrolidone such as those containing vinyl acetate, dimethylaminoethylmethacrylate and quaternary versions of the same with methyl sulfates, and polymers and copolymers of vinyl alcohol and vinyl acetate. Some acrylic polymers include polyacrylic acid, polyacrylamide, copolymers with esters of acrylic acid and methacrylic acid, and copolymers of methylvinylether and maleic anhydride.

Methods for Cleansing the Skin or Hair

The personal cleansing methods of the instant invention are useful for cleansing the skin or hair. Typically, a suitable amount of the cleansing composition is directly applied to the skin or hair to be cleansed, which has optionally been premoistened with water. Alternatively, a suitable amount of the cleansing composition can be applied to the skin or hair to be cleaned via intermediate application to the hands, a washcloth, a sponge, or other application device. It has been found that the compositions of the instant invention provide their optimal cleansing performance when combined with water during the cleansing process. To complete the cleansing process, the compositions of the instant invention are thoroughly rinsed from the skin or hair with water. Suitable amounts of cleansing agent range from, but are not limited to, about 0.5 mg/cm$^2$ to about 5.0 mg/cm$^2$ of skin area or skin area underlying the hair to be cleansed.

Delivery of the Cleansing Product as a Foam

The personal cleansing compositions of the instant invention must be delivered as a foam. Preferably the foam has a density of from about 0.01 gms/cm$^3$ to about 0.25 gms/cm$^3$, more preferably from about 0.05 gms/cm$^3$ to about 0.20 gms/cm$^3$, and most preferably from about 0.08 gms/cm$^3$ to about 0.11 gms/cm$^3$.

For delivery as a foam, the compositions of the instant invention can be delivered, for example, from a hand-held device such as a nonaerosol pump foamer or from an aerosol container charged with a suitable propellant system.

Non-aerosol squeeze foamer packages are well known as exemplified by the disclosures in the following patents that are incorporated herein by reference. U.S. Pat. No. 3,709,437, to Wright, issued Jan. 9, 1973; U.S. Pat. No. 3,937,364, to Wright, issued Feb. 10, 1976; U.S. Pat. No. 4,022,351, to Wright, issued May 10, 1977; U.S. Pat. No. 4,147,306, to Bennett, issued Apr. 3, 1979, U.S. Pat. No. 4,184,615, to Wright, issued Jan. 22, 1980; U.S. Pat. No. 4,598,862, to Rice, issued Jul. 8, 1986; U.S. Pat. No. 4,615,467, to Grogan et al., issued Oct. 7, 1986; and French Patent No. 2,604,622, to Verhulst, published Apr. 8, 1988. These containers (packages) do not use any propellant. The composition is placed in the container reservoir (plastic squeeze bottle). Squeezing the container with the hand forces the composition through a foamer head, or other foam producing means, where the composition is mixed with air and then through a homogenizing means that makes the foam more homogeneous and controls the consistency of the foam. The foam is then discharged as a uniform, non-pressurized aerated foam.

Pressurized aerosol delivery systems are also well-known in the art. When the compositions of the instant invention are delivered from such pressurized systems, the compositions further comprise from about 25% to about 80%, preferably from about 30% to about 50%, of suitable propellants. Examples of such propellants are the chlorinated, fluorinated, and chlorofluorinated lower molecular weight hydrocarbons; nitrous oxide; carbon dioxide; butane; propane; and the like. These propellants are used at a level sufficient to expel the contents of the container.

When the personal cleansing compositions of the instant invention are delivered as a foam, it is preferable that the composition used for such delivery has a viscosity in the range from about 0.1 cPs to about 150 cPs, preferably from about 70 cPs to about 60 cPs, and most preferably from about 20 cPs to about 50 cPs. These viscosities are determined at 25° C. using a Brookfield RVT (Brookfield Instruments, Stoughton, Mass.) equipped with a spindle No. 1 at 100 rpm.

The Squeeze Foamer Container

Squeeze foamer packages are well known as exemplified by the disclosures in the following patents that are incorporated herein by reference. U.S. Pat. Nos.: 3,709,437, Wright, issued Jan. 9, 1973; 3,937,364, Wright, issued Feb. 10, 1976; 4,022,351, Wright, issued May 10, 1977; 4,147,306, Bennett, issued Apr. 3, 1979; 4,184,615, Wright, issued Jan. 22, 1980; 4,598,862, Rice, issued Jul. 8, 1986; and 4,615,467, Grogan et al., issued Oct. 7, 1986; and French Pat. 2,604, 622, Verhulst, published Apr. 8, 1988.

The above containers (packages) do not use any propellant and are therefore safe for the consumer and the environment. The composition is placed in the container reservoir (plastic squeeze bottle). Squeezing the pumping or pressurizing the container with the hand forces the composition through a foamer head, or other foam producing means, where the composition is mixed with air and then through a homogenizing means that makes the foam more homogeneous and controls the consistency of the foam. The foam is then discharged as a uniform, non-pressurized aerated foam.

The minimum pressure to activate the squeeze foamer is about 1 psig, typically from about 2 psig to about 7 psig. The minimum pressure is related to the size of the channels in the dispenser, the viscosity of the composition, etc.

In general, the density of the foam should be between about 0.002 and about 0.25 g/cc, preferably between about 0.05 to about 0.20 g/cc, and more preferably between about 0.05 and about 0.11 g/cc.

Other Product Forms

In addition to the product forms described above, the cleansing compositions of the instant invention can also be suitably formulated as foaming gels, foaming lotions, foaming scrubs, and the like.

Optional Components

The compositions of the present invention can contain optional components such as those conventionally found in personal cleansing products. Conventional antibacterial agents can be included in the present compositions at levels of from about 0.1% to about 4%, preferably from about 0.2% to about 1%. Typical antibacterial agents which are suitable for use herein are 3,4-di- and 3,4',5-tribromosalicylanildes; 4,4'-dichloro-3-(trifluoromethyl)carbanilide; 3,4, 4'-trichlorocarbanilide; phenoxy ethanol or propanol; chlorhexidene salts; hexamidine salts; Irgasan DP 300 (Triclosan); salicylic acid; parachlorometaxylenol; Octopifox; and mixtures of these materials.

Conventional perfumes, dyes, preservatives, and pigments can also be incorporated into compositions of the invention at levels up to about 1.5%. Perfumes are preferably used at levels of from about 0.1% to about 1%, and dyes and pigments are preferably used at levels of from about 0.001% to about 0.5%.

The compositions of the invention can optionally include a hair or skin moisturizer. The preferred level of moisturizer is from about 1% to about 20% by weight. In preferred embodiments, the moisturizer is nonocclusive and is selected from:

1. water-soluble liquid polyols;
2. essential amino acid compounds found naturally occurring in the stratum corneum of the skin; and
3. water-soluble nonocclusives and mixtures thereof.

Some examples of more preferred nonocclusive moisturizers are glycerine, polyethylene glycol, propylene glycol, sorbitol, polyethylene glycol and propylene glycol esters of methyl glucose (e.g. methyl gluxan-20), polyethylene glycol and propylene glycol esters of lanolin alcohol (e.g. Solulan-75), sodium pyrrolidone carboxylic acid, lactic acid, urea, L-proline, guanidine, pyrrolidone and mixtures thereof. Of the above, glycerine is highly preferred.

The compositions of the invention can additionally comprise from about 0.05% to about 5% by weight of hair or skin conditioning agents.

A number of additional optional materials can be added to the compositions of the invention. Such materials include water-soluble sunscreens; keratolytic agents such as salicylic acid; proteins and polypeptides and derivatives thereof; water-soluble or solubilizable preservatives such as Germall 115, methyl, ethyl, propyl and butyl esters of hydroxybenzoic acid, EDTA, Euxyl (RTM) K400, Bronopol (2-bromo-2-nitropropane-1,3-diol); anti-bacterials such as Irgasan (RTM), phenoxyethanol and phenoxypropanol (preferably at levels of from about 0.2% to about 5%); other moisturizing agents such as hyaluronic acid, chitin, and starch-grafted sodium polyacrylates such as Sanwet (RTMO IM-1000, IM-1500 and IM-2500 available from Celanese Superabsorbent Materials, Portsmith, Va., U.S.A. and described in U.S. Pat. No. 4,076,663, incorporated by reference herein; astringents: coloring agents; pearling agents; perfumes and perfume solubilizers etc.

Optional pharmaceutical actives useful in the present invention include any chemical material or compound suitable for topical administration which induces any desired local or systemic effect. These actives are present at a level from about 0.1% to about 20%. Such substances include, but are not limited to antibiotics, antiviral agents, analgesics, antihistamines, antiinflammatory agents, antipruritics, antipyretics, anesthetic agents, diagnostic agents, hormones, antifungals, antimicrobials, cutaneous growth enhancers, pigment modulators, antiproliferatives, antipsoriatics, retinoids, anti-acne medicaments (e.g. benzoyl peroxide, sulfur, etc.), antineoplastics agents, phototherapeutic agents, keratolytics (e.g. resorcinol, salicylic acid) and vitamins.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

EXAMPLE I

A personal cleansing composition is made by combining the following components using conventional mixing techniques:

| Ingredient | % W/W |
| --- | --- |
| Laurdimonium Hydroxyethylcellulose[1] (4% solids) | 20.0 |
| Lauryldimonium Hydroxypropyl Hydrolyzed Collagen[2] (3% solid) | 8.6 |
| Glycerin[3] | 2.0 |
| DMDM Hydantoin (and) Iodopropynyl Butylcarbamate[4] | 0.1 |
| Fragrance[5] | 0.1 |
| Tetrasodium EDETATE[6] | 0.1 |

[1]Available as Crodacel QL (20%).
[2]Available as Lamequat L (35%).
[3]Available as Glycerol.

-continued

| Ingredient | % W/W |
| --- | --- |

[4]Available as Glydant Plus.
[5]Available as Fragrance DL25633.
[6]Available as Na4 EDTA.

The resulting composition is placed in, for example, a squeeze foamer device. Application of approximately 2 grams of the resulting composition having a density of approximately 0.08 gms/cm$^3$ is useful for topical application as a rinse-off cleanser to remove, for example, dirt and oil as well as difficult to remove make-up, waterproof mascara and the like.

EXAMPLE II

A personal cleansing composition is made by combining the following components using conventional mixing techniques:

| Ingredient | % W/W |
| --- | --- |
| Laurdimonium Hydroxyethylcellulose (4% solids) | 20.0 |
| Lauryldimonium Hydroxypropyl Hydrolyzed Collagen (2.25% solid) | 6.43 |
| Hydroxyethylcellulose[1] | 0.1 |
| Polyquaternium 4[2] | 0.075 |
| Glycerin | 2.0 |
| DMDM Hydantoin (and) Iodopropynyl Butylcarbamate | 0.1 |
| Fragrance | 0.1 |
| Tetrasodium EDETATE | 0.1 |
| Aloe Vera Gel[3] | 1.25 |

[1]Available as Natrosol 250 HHR.
[2]Available as Celquat L-200.
[3]Available as Aloe Vera Gel 10X.

The resulting composition is placed in, for example, a squeeze foamer device. Application of approximately 2 grams of the resulting composition having a density of approximately 0.08 gms/cm$^3$ is useful for topical application as a rinse-off cleanser to remove, for example, dirt and oil as well as difficult to remove make-up, waterproof mascara and the like.

EXAMPLE III

A personal cleansing composition is made by combining the following components using conventional mixing techniques:

| Ingredient | % W/W |
| --- | --- |
| Water | q.s. |
| Laurdimonium Hydroxyethylcellulose (4.25% solids) | 12.14 |
| Hydroxyethylcellulose | 0.3 |
| Polyquaternium 24[1] | 1.45 |
| Glycerin | 1.25 |
| Hexylene Glycol[2] | 5.0 |
| DMDM Hydantoin (and) Iodopropynyl Butylcarbamate | 0.1 |
| Fragrance | 0.1 |
| Tetrasodium EDETATE | 0.1 |
| Panthenol[3] | 0.75 |

[1]Available as Quatrisolft LM200.
[2]Available as Hexylene Glycol.
[3]Available as dl-Panthenol.

The resulting composition is placed in, for example, a squeeze foamer device. Application of approximately 2 grams of the resulting composition having a density of approximately 0.08 gms/cm$^3$ is useful for topical application as a rinse-off cleanser to remove, for example, dirt and oil as well as difficult to remove make-up, waterproof mascara and the like.

EXAMPLE IV

A personal cleansing composition is made by combining the following components using conventional mixing techniques:

| Ingredient | % W/W |
| --- | --- |
| Water | q.s. |
| 2-Phenylbenzimidazole-5-Sulfonic Acid[1] | 4.0 |
| Laurdimonium Hydroxyethylcellulose (2% solids) | 10.0 |
| Lauryldimonium Hydroxypropyl Hydrolyzed Collagen (2.25% solid) | 6.43 |
| Hydroxyethylcellulose | 0.20 |
| Polyquaternium | 0.15 |
| Glycerin | 3.0 |
| DMDM Hydantoin (and) Iodopropynyl Butylcarbamate | 0.1 |
| Fragrance | 0.1 |
| Tetrasodium EDETATE | 0.1 |
| Panthenol | 0.75 |

[1]Available as Eusolex 232.

The resulting composition is placed in, for example, a squeeze foamer device. Application of approximately 2 grams of the resulting composition having a density of approximately 0.08 gms/cm$^3$ is useful for topical application as a rinse-off cleanser to remove, for example, dirt and oil as well as difficult to remove make-up, waterproof mascara and the like.

EXAMPLE V

A personal cleansing composition is made by combining the following components using conventional mixing techniques:

| Ingredient | % W/W |
| --- | --- |
| Water | q.s. |
| Cyclomethicone[1] | 2.0 |
| Dimethicone[2] | 3.0 |
| Laurdimonium Hydroxyethylcellulose (3.25% solids) | 16.25 |
| Lauryldimonium Hydroxypropyl Hydrolyzed Collagen (2.25% solid) | 6.43 |
| Polyquaternium 4 | 0.15 |
| Glycerin | 7.0 |
| DMDM Hydantoin (and) Iodopropynyl Butylcarbamate | 0.1 |
| Fragrance | 0.1 |
| Tetrasodium EDETATE | 0.1 |
| Aloe Vera Gel | 1.25 |

[1]Available as DC 344 Fluid.
[2]Available as DC 225 Fluid.

The resulting composition is placed in, for example, a squeeze foamer device. Application of approximately 2 grams of the resulting composition having a density of approximately 0.08 gms/cm$^3$ is useful for topical application as a rinse-off cleanser to remove, for example, dirt and oil as well as difficult to remove make-up, waterproof mascara and the like.

EXAMPLE VI

A personal cleansing composition is made by combining the following components using conventional mixing techniques:

| Ingredient | % W/W |
| --- | --- |
| Water | q.s. |
| Alcohol | 8.0 |
| Witch Hazel | 1.5 |
| Laurdimonium Hydroxyethylcellulose (1.75% solids) | 8.75 |
| Laurdimonium Hydroxpropyl Hydrolyzed Collagen (2.25% solid) | 6.43 |
| Polyquaternium 4 | 0.15 |
| DMDM Hydantoin (and) Iodopropynyl Butylcarbamate | 0.1 |
| Fragrance | 0.1 |
| Tetrasodium EDETATE | 0.1 |
| Aloe Vera Gel | 0.25 |

The resulting composition is placed in, for example, a squeeze foamer device. Application of approximately 2 grams of the resulting composition having a density of approximately 0.08 gms/cm$^3$ is useful for topical application as a rinse-off cleanser to remove, for example, dirt and oil as well as difficult to remove make-up, waterproof mascara and the like.

What is claimed is:

1. A method for personal cleansing comprising applying to the skin or hair an aerated rinse-off cleansing composition substantially-free of a surfactant comprising:
   (a) from about 0.01% to about 20% by weight of a viscosity enhancing water-soluble cationic polymer having a molecular weight of from about 1,000 to about 3,000,000 wherein said viscosity enhancing polymer accounts for a rise in the viscosity of the composition, without the polymer, of at least about 1 centipoise, and
   (b) from about 20% by weight to about 99.8% by weight of water.

2. A method according to claim 1 wherein said composition is delivered from a non-aerosol mechanical pump such that said cleansing composition is delivered as an aerated foam having a density of from about 0.01 gms/cm$^3$ to about 0.25 gms/cm$^3$ and wherein said water-soluble polymer has a molecular weight of from about 1,000 to about 150,000.

3. A method according to claim 2 wherein said density is from about 0.08 gms/cm$^3$ to about 0.11 gms/cm$^3$.

4. A method according to claim 1 wherein said composition is delivered from an aerosol container which further comprises a propellant gas such that said cleansing composition is delivered as a foam having a density of from about 0.01 gms/cm$^3$ to about 0.25 gms/cm$^3$.

5. A method according to claim 4 wherein said density is from about 0.08 gms/cm$^3$ to about 0.11 gms/cm$^3$.

6. A method according to claim 2 wherein the composition comprises from about 2.0% to about 12.0% by weight of at least one cationic polymer.

7. A method according to claim 6 wherein the cationic polymer is selected from the group consisting of laurdimonium hydroxyethyl cellulose, lauryldimonium hydroxypropyl hydrolyzed casein, lauryldimonium hydroxypropyl hydrolyzed collagen, lauryldimonium hydroxypropyl hydrolyzed keratin, lauryldimonium hydroxypropyl hydrolyzed silk, lauryldimonium hydroxypropyl hydrolyzed soy protein, polyquaternium-11, and mixtures thereof.

8. A method according to claim 7 wherein the cationic polymer is selected from the group consisting of laurdimonium hydroxyethyl cellulose, lauryldimonium hydroxypropyl hydrolyzed collagen, and mixtures thereof.

9. A method according to claim 8 wherein the cationic polymer comprises a mixture of laurdimonium hydroxyethyl cellulose and lauryldimonium hydroxypropyl hydrolyzed collagen in a weight ratio of approximately 2:1 to about 1:1.

10. A method according to claim 9 which further comprises from about 0.5% by weight to about 5% by weight of a humectant.

11. A method according to claim 9 which further comprises from about 0.1–2% by weight of a anti-acne active.

12. A method according to claim 11 wherein said anti-acne active is salicylic acid.

13. A method according to claim 9 which further comprises from about 0.1–20% by weight of an astringent.

14. A method according to claim 10 wherein said humectant is a $C_3$–$C_6$ diol or triol.

15. A method according to claim 14 wherein said humectant is glycerol.

16. A method according to claim 11 wherein said composition has a viscosity of from about 0.1 cPs to about 150 cPs 25° C., Brookfield RVT, Spindle No. 1, at 100 rpm.

17. A method according to claim 13 wherein said composition has a viscosity of from about 20 cPs to about 50 cPs.

\* \* \* \* \*